US006928857B1

(12) United States Patent
Brown

(10) Patent No.: US 6,928,857 B1
(45) Date of Patent: Aug. 16, 2005

(54) APPARATUS FOR CONTINUOUS MEASUREMENT OF ROAD SURFACE FRICTION

(76) Inventor: Glen A. J. Brown, 8821-8th Avenue, S.W., Edmonton, Alberta (CA) T6K 1C4

( * ) Notice: Subject to any disclaimer, the term of this patent is extended or adjusted under 35 U.S.C. 154(b) by 0 days.

(21) Appl. No.: 10/890,511

(22) Filed: Jul. 14, 2004

(51) Int. Cl.[7] ............................................. G01N 19/02
(52) U.S. Cl. ................................................... 73/9
(58) Field of Search ................................................ 73/9

(56) References Cited

U.S. PATENT DOCUMENTS

| | | | | |
|---|---|---|---|---|
| 2,496,405 | A | * | 2/1950 | Foufounis ........................ 73/9 |
| 2,690,668 | A | | 10/1954 | Lucas |
| 3,301,039 | A | * | 1/1967 | Kummer .......................... 73/9 |
| 3,332,276 | A | * | 7/1967 | Clarke ............................. 73/9 |
| 3,367,170 | A | * | 2/1968 | Lynch et al. ..................... 73/9 |
| 3,538,742 | A | | 11/1970 | Benning |
| 4,050,290 | A | | 9/1977 | Lonnroth |
| 4,098,111 | A | * | 7/1978 | Hardmark et al. .............. 73/9 |
| 4,144,748 | A | * | 3/1979 | Vinogradov et al. .......... 73/146 |
| 4,662,211 | A | * | 5/1987 | Strong ............................ 73/9 |
| 4,909,073 | A | * | 3/1990 | Takahashi et al. ............ 73/146 |
| 4,955,933 | A | * | 9/1990 | Sistonen ......................... 73/9 |
| 4,958,512 | A | * | 9/1990 | Johnsen .......................... 73/9 |
| 6,192,736 | B1 | * | 2/2001 | Clem .............................. 73/9 |
| 6,276,189 | B1 | * | 8/2001 | Hurson ........................... 73/9 |
| 6,427,519 | B2 | * | 8/2002 | Ueda et al. ..................... 73/9 |
| 6,463,784 | B2 | * | 10/2002 | Kashiwagi et al. ............. 73/9 |
| 6,525,671 | B1 | * | 2/2003 | Vannan ...................... 340/901 |
| 6,681,614 | B1 | * | 1/2004 | Riffe .............................. 73/9 |
| 6,840,098 | B2 | * | 1/2005 | Halliday ..................... 73/146 |
| 2003/0159494 | A1 | * | 8/2003 | Klovning ........................ 73/9 |

FOREIGN PATENT DOCUMENTS

| | | | | | |
|---|---|---|---|---|---|
| JP | | 04102034 | A | * 4/1992 | ............ G01L 5/00 |
| JP | | 06167439 | A | * 6/1994 | ......... G01N 19/02 |

* cited by examiner

Primary Examiner—Hezron Williams
Assistant Examiner—John Fitzgerald
(74) Attorney, Agent, or Firm—Adrian D. Battison; Michael R. Williams; Ryan W. Dupuis

(57) ABSTRACT

A method and apparatus for continuously or at a rapid rate of repetition measuring friction between a road surface and a tire, especially suitable for evaluating the severity of visually undetectable road ice at traffic speeds, consists of a separate test wheel attached to a vehicle and in contact with a road surface, wherein a controlled slippage of test wheel is created by a compressed spring acting either clockwise or counterclockwise to a hinge with a substantially vertical axis upon which the test wheel arm pivots. Electrical signals are produced varying in accordance with the angle of yaw, the signals being transmitted to an onboard computer or remote receiver. A suspension system links the test wheel to the vehicle.

10 Claims, 5 Drawing Sheets

Left side view

Direction of vehicle travel

Left side view

Left side view

APPARATUS FOR CONTINUOUS MEASUREMENT OF ROAD SURFACE FRICTION

This invention relates to an apparatus for providing an indication to a vehicle operator of a co-efficient of friction of a road surface.

BACKGROUND OF THE INVENTION

The presence of ice on the road is a factor in many traffic accidents thus the availability of continuous information representative of the co-efficient of friction between a tire and a road surface can be of significant benefit to drivers of moving vehicles. A display or audible signal indicating the extent of reduced tire adhesion can advise drivers when road conditions change in a manner that is not visually noticeable.

Related devices for U.S. Pat. No. 2,690,668 to Lucas, U.S. Pat. No. 3,538,742 to Benning, U.S. Pat. No. 4,050,290 to Lonnroth.

In order to accurately measure road friction it is preferable to create slip between the tire and the road surface. One means of creating slip is an accelerating or decelerating force applied to a test wheel aligned with the path of travel. Many devices provide intermittent as opposed to continuous measurement due to the pulsed application of braking. In certain other devices, a velocity differential of the tire circumference in relation to the road surface at the point of contact is created. Vehicles using such methods have inevitable scrubbing of the tire, or there is a sacrifice made in the accuracy of the friction measurement to prolong the tire life. Other devices collect data from the four load-bearing wheels of the automobile however such systems cannot provide continuous accurate measurements unless a braking or accelerating force is applied.

The current invention provides continuous measurement capability while reducing the slippage of the tire to a very low rate since the velocity difference between the contact patch of the tire and the point of contact with the surface being tested is minimal. The current invention provides an acceptable test tire mileage, very little effect on vehicle steering, very little effect upon vehicle maximum traveling speed, and very little effect upon fuel efficiency of the carrier vehicle. Although loose snow, rough roads, and other factors may affect accuracy, the invention provides very good consistency in readings at all speeds.

Devices have previously been provided that incorporate a single test wheel set at an angle of yaw i.e. toe-in or toe-out, to impart a measurable force on a load cell or other electronic instrument. The previous devices have been deficient in suspension, especially with respect to the 'range of travel' necessary to operate reliably on rough or potholed roads at the speed of highway traffic. Other devices require more than one wheel, a design that is not readily adapted to lighter vehicles traveling at highway speeds.

SUMMARY OF THE INVENTION

It is one object of the present invention to provide an improved apparatus for detecting the co-efficient of friction of a road surface.

According to the present invention there is provided an apparatus for measuring the co-efficient of friction of a paved road surface comprising:

a test wheel for rolling on the paved road surface;

a primary frame arranged to be attached to a road transportation vehicle moving along a direction of travel at a location thereon such that the test wheel can roll on the road surface as the vehicle moves in a forward direction over the road surface;

an intermediate component pivotally connected to said primary frame by a first swivel connection;

a suspension arm pivotally connected to said intermediate component by a second swivel connection and trailing rearwardly and downwardly therefrom relative to the direction of forward movement of the vehicle;

said first swivel connection defining a generally upright swivel axis allowing said intermediate component to swivel about said upright axis in response to a torque applied to said suspension arm about the upright axis;

said second swivel connection defining a substantially horizontal pivot axis allowing said suspension arm to pivot about the horizontal pivot axis in an ascending or descending direction;

the test wheel being rotatably mounted on a trailing end of said suspension arm for rotation of the test wheel about a horizontal rotation axis parallel to said horizontal pivot axis so that the test wheel lies in a wheel plane at right angles to the axis;

a first spring applying a spring force between the primary frame and said intermediate component about said generally upright axis of rotation tending to rotate said intermediate component and said test wheel carried thereby around the axis to a position defining for the wheel plane of the test wheel an angle of yaw relative to a direction plane containing the direction of travel of the vehicle, such that, when the vehicle is traveling along the direction plane with adequate co-efficient of friction, the test wheel tends to lie with the wheel plane parallel to the direction plane and, when the co-efficient of friction is reduced, the wheel plane tends to revert to the angle of yaw;

a sensor responsive to changes in the angle between the direction plane and the wheel plane;

and a display for displaying to an operator of the vehicle data related to the changes in angle detected by the sensor so as to provide to the operator information concerning the co-efficient of friction.

Preferably the display comprises a gauge, computer and wireless electronic transmitter connected to said sensor to display, record, and transmit said measurements to a remote location.

Preferably the first spring is connected directly between the intermediate component and the primary frame.

Preferably there is provided a second spring located between said primary frame and said intermediate component acting on said intermediate component in the opposite direction to said first spring, providing a progressive resistance to rotation of said intermediate component in either a clockwise or a counterclockwise direction from a neutral or equilibrium position causing said intermediate component to return to the same position after an external lateral force is applied and removed.

Preferably there is provided an adjustment member connected between a spring retainer of the first spring and the primary frame to set the test wheel at a required angle of yaw and to adjust spring modulus.

Preferably the adjustment member comprises a threaded bolt.

Preferably the adjustment member comprises a first threaded bolt and nut, the head of said bolt attached to a pivoting connection on said main mounting bracket, and the shaft of said bolt aligned tangential to a circle with center coincident to said vertical axis of rotation, said bolt shaft passing through a bracket on said intermediate component, then through said first coil spring, said coil spring mounted on said intermediate component aligned tangential to said circle, said bolt shaft passing through the spring retainer of said spring, said nut being threaded onto said bolt shaft and tightened against said retainer and a second threaded bolt and nut similarly mounted to said main mounting bracket and passing through a second coil spring, said second coil spring being mounted to act upon said intermediate component in the opposite direction of rotation as said first coil spring.

Preferably there is provided a spring and shock absorber acting in a vertical plane mounted between the intermediate component and the suspension arm to impede the velocity and vertical deviation during a vertical bounce and rebound cycle of the test wheel.

Preferably there is provided a shock absorber mounted to act horizontally between the primary frame and the intermediate component to impede the velocity and horizontal deviation during a bounce and rebound cycle of the test wheel caused by impacts to the test wheel.

The present invention relates to a friction measuring apparatus that is incorporated in a motor vehicle, to a large extent enabling automatic measuring methods, and is especially advantageous for measurements on paved surfaces while traveling at the speed of highway traffic. The measuring apparatus includes a single test wheel attached to a vehicle used in road transportation, said wheel engaging the road surface during measuring operations at a slight angle of yaw and retractable when not required, a trailing suspension arm, an intermediate component between the wheel and the vehicle allowing movement of the trailing suspension arm about both a vertical axis of rotation and about a horizontal axis of rotation, a spring mounted to pull or push the hinged component to establish the angle of yaw, a sensor mounted at a given radius from the vertical axis of rotation to measure the change in the angle of rotation of the intermediate component.

In the operational mode, the test wheel is attached to the suspension arm with its alignment intersecting the vertical pivotal axis between the suspension arm and the vehicle, an arrangement that allows the friction at the contact patch of the tire on the road to force the test wheel toward an angle of yaw of zero degrees. The greater the co-efficient of friction, the greater the centering force. The force of the horizontal spring resists the centering force caused by friction. The change in the angle of yaw is dependent upon the change in the co-efficient of friction.

In a preferred embodiment of the device, the change in the angle of yaw is measured indirectly by a force measurement taken by a load cell connected between the mounting frame and a horizontal spring, the spring being attached to the intermediate component. The load cell is connected to a battery-powered computer through a digital display. The computer or display are set to emit visual or audible signals when the received values exceed or drop below specified ranges.

The entire scope of the present invention will become apparent from the following description and reference to the accompanying drawings. It should be understood, however, that the description and the specific examples while indicating preferred embodiments, are given by way of illustration only, since various changes and modifications within the spirit and scope of the invention will become apparent as the description herein progresses.

DESCRIPTION OF THE PREFERRED EMBODIMENTS

The preferred embodiments are now described in detail with reference to the relevant drawings.

Figure 1:
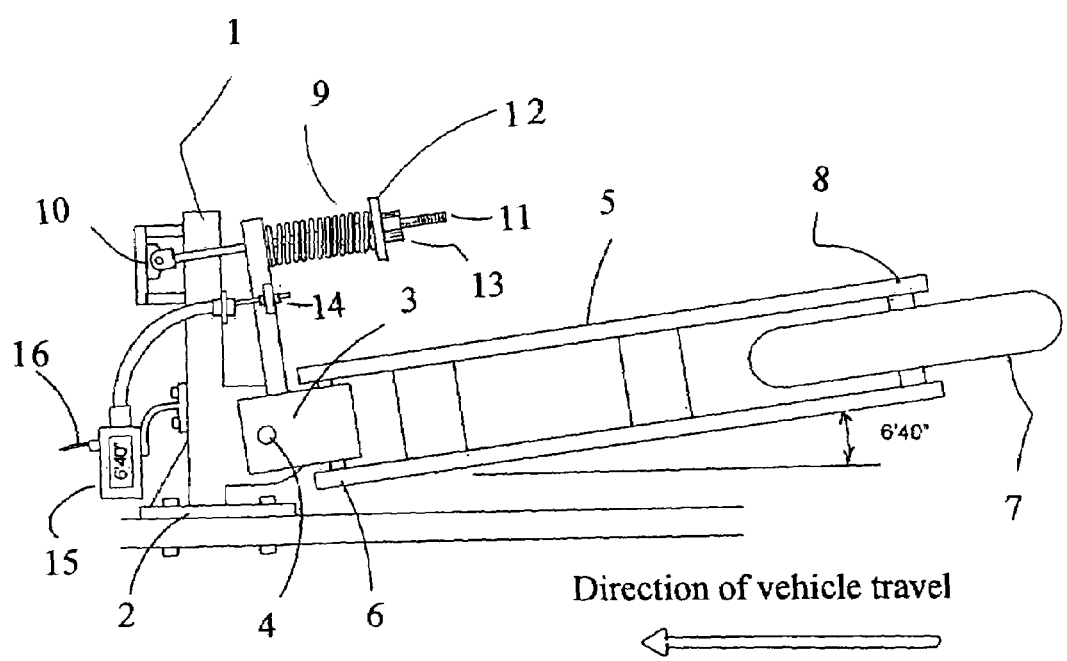
FIG. 1 is a plan view of a first embodiment of the invention.

FIG. 1 is a plan view of one of the preferred embodiments. The primary frame 1 which serves to mount the apparatus to a transport vehicle is mounted to the chassis or other structurally sound component of the vehicle by a mounting bracket 2. The primary frame 1 is pivotally connected to the intermediate component 3 by a shaft and bearing assembly 4 with substantially vertical axis. The intermediate component 3 is connected to the suspension arm 5 by a shaft and bearing assembly 6 with substantially horizontal axis. The test wheel with pneumatic tire 7 is rotatably mounted on the suspension arm 5 by a high speed axle assembly 8 with the test wheel's alignment lying along a radial line from the vertical shaft 4.

A horizontal spring 9 becomes partially compressed and exerts a moment on the intermediate component 3 when the vehicle is in forward motion. The tensioning threaded rod 11 is mounted to the primary frame 1 by a pin connection 10. The spring 9 is held against the intermediate component 3 by a spring retainer 12 and a threaded nut 13 on the threaded rod 11. Tightening or loosening the nut 13 changes the angle of yaw of the test wheel 7 when testing. A flexible cable in a cable housing 14 is mounted between the primary frame 1 and the intermediate frame 3 to detect relative movement of these components. An electronic linear scale 15 measures the movement of the cable and the measurements are transmitted at a specified rate of repetition to a computer by an electrical cable 16.

Figure 2:
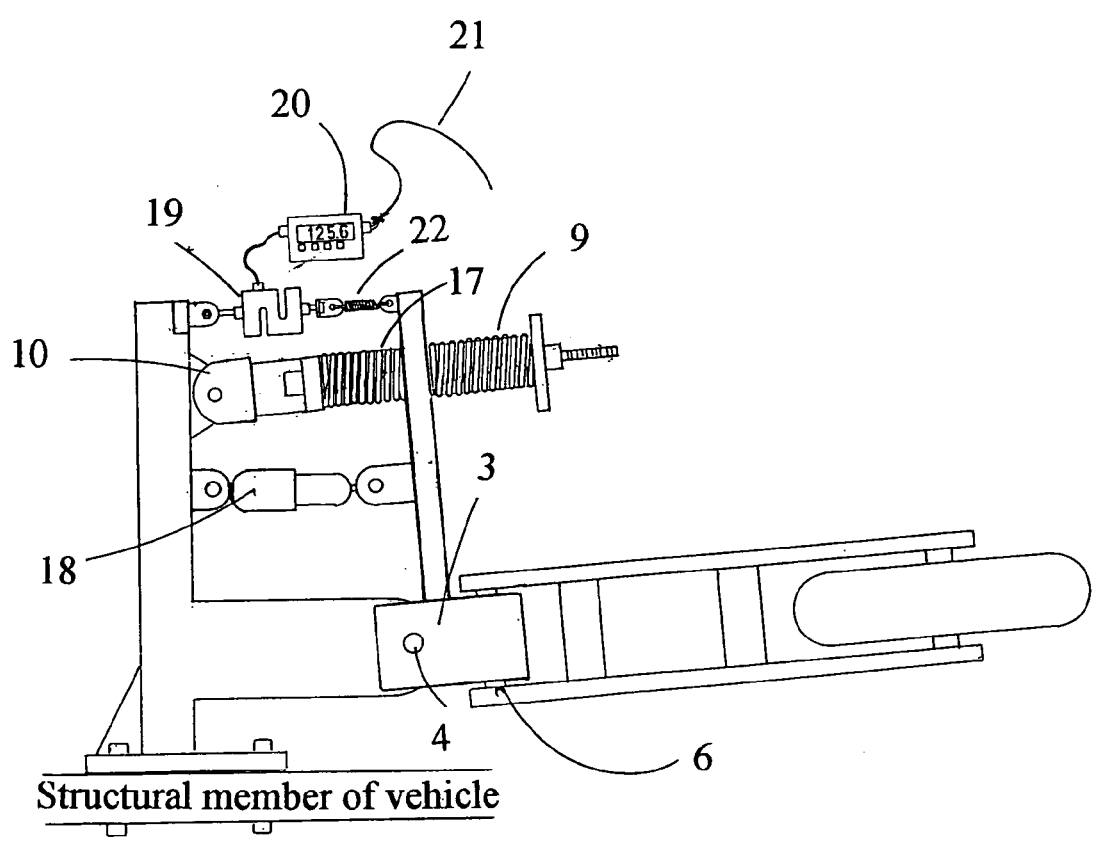
FIG. 2 is a plan view of a second embodiment of the invention.

FIG. 2 is a plan view of a second embodiment showing the same intermediate component 3 as shown in FIG. 1. The vertical shaft and bearing assembly 4 and horizontal shaft and bearing assembly 6 are quite similar to FIG. 1. The most important difference between the embodiments shown in FIG. 1 and FIG. 2 is the addition of a second spring 17. The second spring 17 is mounted in a manner to exert a moment about the vertical shaft, however this moment is exerted in the opposite direction from the moment exerted by the first spring 9. This arrangement of two springs restricts the range of movement laterally of the test wheel while absorbing sudden side forces. The nut on the threaded rod holding the first spring 9 and the second spring 17 can be used to increase preload compression of the springs and hence the spring modulus, as well as adjust the angle of yaw of the test wheel. The angle of yaw may be changed independently while leaving the preload unchanged if the pin connection 10 for the threaded rod is mounted on a moveable bracket. A moveable bracket is not shown since there are several possible methods of adjustment, for example, a screwed movement, a sliding movement, a hinged movement. Any of these methods would work equally well.

FIG. 2 also shows a first shock absorber 18 acting in a horizontal plane and tangential to a radius from the vertical swivel axis 4. A dampening device is desirable to dampen and moderate side-to-side movement of the test wheel.

FIG. 2 shows an alternate sensor arrangement for producing electronic measurement data. The measurement of the angle of rotation of the intermediate component 3 is accomplished in this embodiment by a load cell 19 mounted between the intermediate component and the primary frame. A third spring 22, smaller than the first spring 9 and second spring 17, is connected in series with the load cell 19. The force measured by the load cell 19 is therefore dependent upon the angle of rotation of the intermediate component about the vertical swivel axis 4 as well as being dependent upon the initial tension in the spring 22 and the spring modulus of the spring 22. The load cell 19 transmits an electrical signal to a force gauge with display 20 which processes the signal and sends the measurements to a computer via a cable 21 or wireless connection. In addition to the visible display of measurements on the gauge, the computer may produce a visual display or audible warning as well as recording and transmitting data to remote locations through wireless communications.

Figure 3:
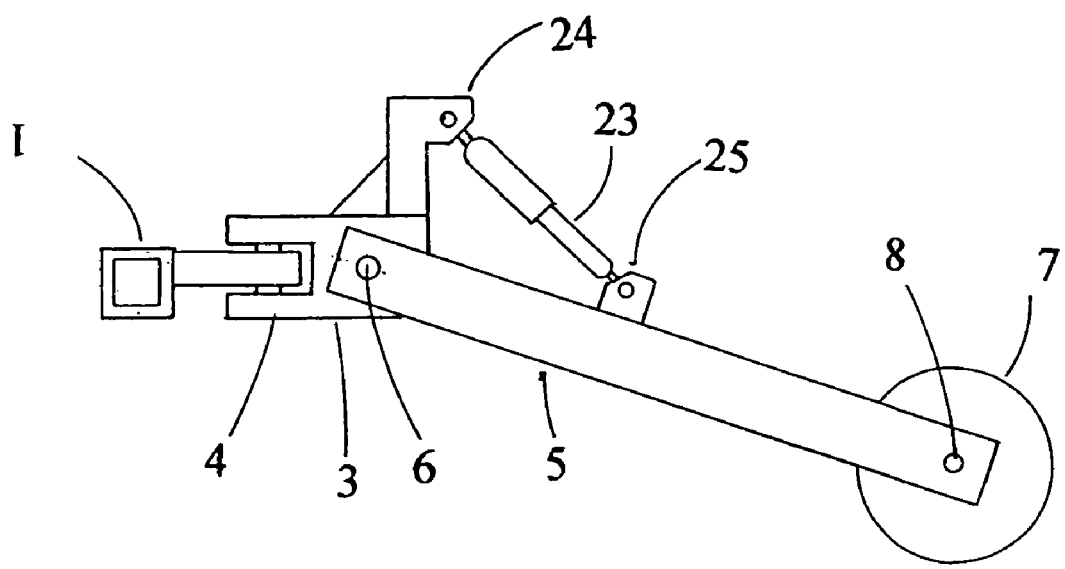
FIG. 3 is a left side elevation view of the embodiments of FIG. 1 and FIG. 2.

FIG. 3 shows a left side elevation view of the first embodiment and second embodiment in which a second shock absorber 23 acts in a vertical plane and tangential to the horizontal swivel axis 6. This view serves to show the relative positions of the primary frame 1, the intermediate component 3, the vertical swivel axis 4, the suspension arm 5, the horizontal swivel axis 6, the shock absorber mount 24 on the intermediate component, and the shock absorber mount 25 on the suspension arm.

Figure 4:
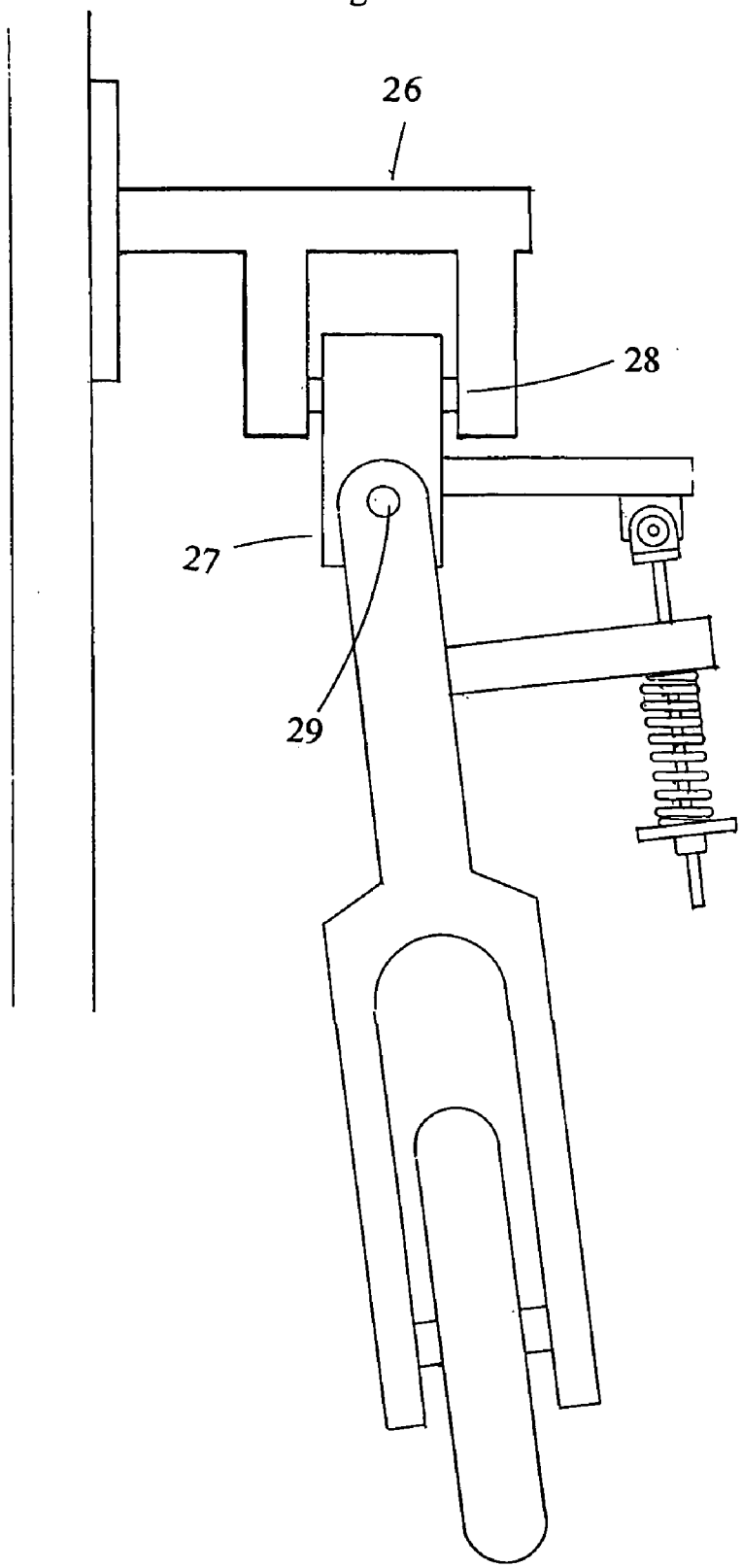
FIG. 4 is a plan view of a third embodiment.

FIG. 4 is a plan view of a third embodiment of the invention. This embodiment differs from the first and second embodiments due to the vertical swivel axis and horizontal swivel axis being interchanged. The primary frame 26 attaches to the vehicle in a similar manner however the primary frame is linked to the intermediate component 27 by a shaft and bearing assembly 28 with a horizontal swivel axis which is parallel to the rear axle of the transport vehicle. The suspension arm is linked to the intermediate component 27 by a shaft and bearing assembly 29 with a vertical swivel axis.

Figure 5:
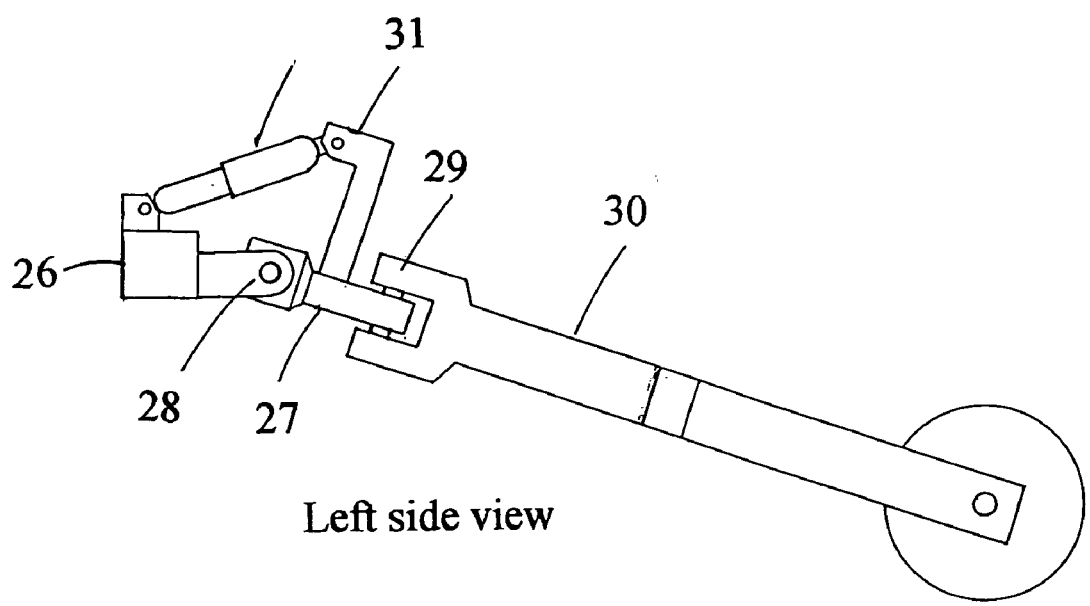
FIG. 5 is a left side elevation view of the embodiment of FIG. 4.

FIG. 5 is a left side elevation view of the embodiment shown in FIG. 4. This view serves to show the position of the shock absorber mount 31 on the intermediate component 27. In the third embodiment of the invention, the primary frame 26 can be readily adapted to provide a means for pulling the shock absorber tower 31 forward and thus raising the test wheel to a storage position when it is not in use. This convenience is found in the third embodiment only. In FIG. 5, the measurements are taken differently. They must indicate the rotation of the suspension arm about the axis 29.

The drawings, while not specifying exact dimensions and geometry, show the essential parts of the invention and the arrangements of these parts that have been found to produce acceptable results. Various arrangements of horizontal springs 9 and 17 shown in FIG. 2 have been found to work equally well. The location may vary as long as the required moment is imparted to the intermediate component about the vertical swivel axis 4. Each of the two springs 9 and 17 may be mounted using separate threaded rods and thus permit a wide range of combinations of yaw angle and spring preload. Coil springs may be substituted by torsion or other springs.

Accuracy of friction measurements is largely dependent upon the design factors such as the weight on the test wheel, tire characteristics, moment of inertia, spring modulus and dampening. In this respect, the sensor is only one of many factors and therefore it may be a linear scale, force gauge, or rotary encoder, as long as the measurements directly or indirectly indicate the rotation of the intermediate component about the vertical swivel axis 4 in FIG. 1.

There are available instruments for reading the angular rotation directly but this is not necessary. The sensors indicated in FIGS. 1 and 2 respond to linear movement along a chord or tangent rather than angular movement. Accordingly the relationship between the readings and the angular rotation will not be exactly proportional. For this application the accuracy is sufficient. The sensor is mounted at a sufficient radius from the vertical swivel axis, and the angular rotation is sufficiently small, so the change in distance along a tangent or chord of the circle is closely proportional to the angular rotation.

The embodiments described typically are used in conjunction with an electronic display and computer to provide the driver with real time information and, when desired, to make a graphical record of the friction measurements.

The measurements of change in the angle of rotation can be converted into co-efficient of friction, skid resistance, or estimated vehicle stopping distance, by making up tables through experimentation. Either force or linear measurements may be used to find the change in the angle of rotation. The force (load cell) measurements vary according to the compression in the spring which is a function of the angle of rotation. The linear scale measurements are taken along a chord of a circle with center on the vertical axis of rotation. The change in linear distance along a chord is proportional to the change in the angle of rotation.

What is claimed is:

1. An apparatus for measuring the co-efficient of friction of a paved road surface comprising:
    a test wheel for rolling on the paved road surface;
    a primary frame arranged to be attached to a road transportation vehicle moving along a direction of travel at a location thereon such that the test wheel can roll on the road surface as the vehicle moves in a forward direction over the road surface;
    an intermediate component pivotally connected to said primary frame by a first swivel connection;
    a suspension arm pivotally connected to said intermediate component by a second swivel connection and trailing rearwardly and downwardly therefrom relative to the direction of forward movement of the vehicle;
    said first swivel connection defining a generally upright swivel axis allowing said intermediate component to swivel about said upright axis in response to a torque applied to said suspension arm about the upright axis;
    said second swivel connection defining a substantially horizontal pivot axis allowing said suspension arm to pivot about the horizontal pivot axis in an ascending or descending direction;
    the test wheel being rotatably mounted on a trailing end of said suspension arm for rotation of the test wheel about a horizontal rotation axis parallel to said horizontal pivot axis so that the test wheel lies in a wheel plane at right angles to the axis;
    a first spring applying a spring force between the primary frame and said intermediate component about said generally upright axis of rotation tending to rotate said intermediate component and said test wheel carried thereby around the axis to a position defining for the wheel plane of the test wheel an angle of yaw relative to a direction plane containing the direction of travel of the vehicle, such that, when the vehicle is traveling along the direction plane with adequate co-efficient of friction, the test wheel tends to lie with the wheel plane parallel to the direction plane and, when the co-efficient of friction is reduced, the wheel plane tends to revert to the angle of yaw;

a sensor responsive to changes in the angle between the direction plane and the wheel plane;

and a display for displaying to an operator of the vehicle data related to the changes in angle detected by the sensor so as to provide to the operator information concerning the co-efficient of friction.

2. The apparatus according to claim 1 wherein the display comprises a gauge, computer and wireless electronic transmitter connected to said sensor to display, record, and transmit said measurements to a remote location.

3. The apparatus according to claim 1 wherein the first spring is connected directly between the intermediate component and the primary frame.

4. The apparatus according to claim 1 wherein there is provided a second spring located between said primary frame and said intermediate component acting on said intermediate component in the opposite direction to said first spring, providing a progressive resistance to rotation of said intermediate component in either a clockwise or a counterclockwise direction from a neutral or equilibrium position causing said intermediate component to return to the same position after an external lateral force is applied and removed.

5. The apparatus according to claim 1 wherein there is provided a spring and shock absorber acting in a vertical plane mounted between the intermediate component and the suspension arm to impede the velocity and vertical deviation during a vertical bounce and rebound cycle of the test wheel.

6. The apparatus according to claim 1 wherein there is provided a shock absorber mounted to act horizontally between the primary frame and the intermediate component to impede the velocity and horizontal deviation during a bounce and rebound cycle of the test wheel caused by impacts to the test wheel.

7. The apparatus according to claim 1 wherein there is provided an adjustment member connected between a spring retainer of the first spring and the primary frame to set the test wheel at a required angle of yaw and to adjust spring modulus.

8. The apparatus according to claim 7 wherein the adjustment member comprises a threaded bolt.

9. The apparatus according to claim 7 wherein the adjustment member comprises a first threaded bolt and nut, the head of said bolt attached to a pivoting connection on said primary frame, and the shaft of said bolt aligned tangential to a circle with center coincident to said vertical axis of rotation, said bolt shaft passing through a bracket on said intermediate component, then through said first coil spring, said coil spring mounted on said intermediate component aligned tangential to said circle, said bolt shaft passing through the spring retainer of said spring, said nut being threaded onto said bolt shaft and tightened against said retainer and a second threaded bolt and nut similarly mounted to said primary frame and passing through a second coil spring, said second coil spring being mounted to act upon said intermediate component in the opposite direction of rotation as said first coil spring.

10. An apparatus for measuring the co-efficient of friction of a paved road surface comprising:

a test wheel for rolling on the paved road surface;

a primary frame arranged to be attached to a road transportation vehicle;

an intermediate component pivotally connected to said primary frame by a first swivel connection;

a suspension arm pivotally connected to said intermediate component by a second swivel connection and trailing rearwardly therefrom relative to the direction of forward movement of the vehicle;

said first swivel connection defining a horizontal swivel axis parallel to the rear wheel axles of said transportation vehicle;

said second swivel connection defining a generally upright swivel axis when said test wheel is in position for testing the road surface;

a first spring applying a spring force between said intermediate component and said suspension arm about said generally upright axis of rotation tending to rotate said suspension arm and said test wheel carried thereby around the axis to a position defining for the wheel plane of the test wheel an angle of yaw relative to a direction plane containing the direction of travel of the vehicle;

a sensor responsive to changes in the angle between the direction plane and the wheel plane;

and a display for displaying to an operator of the vehicle data related to the changes in angle detected by the sensor so as to provide to the operator information concerning the co-efficient of friction.

* * * * *